United States Patent
Schmidt et al.

(10) Patent No.: US 9,164,024 B2
(45) Date of Patent: Oct. 20, 2015

(54) HYBRID, PLANAR OPTOFLUIDIC INTEGRATION

(75) Inventors: Holger Schmidt, Capitola, CA (US); Aaron Roe Hawkins, Provo, UT (US)

(73) Assignees: The Regents of the University of California, Oakland, CA (US); Brigham Young University, Provo, UT (US)

(*) Notice: Subject to any disclaimer, the term of this patent is extended or adjusted under 35 U.S.C. 154(b) by 82 days.

(21) Appl. No.: 13/988,253

(22) PCT Filed: Nov. 18, 2011

(86) PCT No.: PCT/US2011/061463
§ 371 (c)(1),
(2), (4) Date: May 17, 2013

(87) PCT Pub. No.: WO2012/068499
PCT Pub. Date: May 24, 2012

(65) Prior Publication Data
US 2014/0111800 A1    Apr. 24, 2014

Related U.S. Application Data

(60) Provisional application No. 61/415,467, filed on Nov. 19, 2010.

(51) Int. Cl.
*G01N 21/00* (2006.01)
*G01J 1/42* (2006.01)
(Continued)

(52) U.S. Cl.
CPC .......... *G01N 21/01* (2013.01); *B01L 3/502761* (2013.01); *G01N 21/0303* (2013.01);
(Continued)

(58) Field of Classification Search
CPC ........... G01N 21/0303; G01N 21/7703; B01L 3/502761; B01L 2200/0647; B01L 2300/0822; B01L 2200/0668; B01L 2300/0877; Y10T 29/49826

USPC ............ 356/246, 432–440; 29/428; 250/373, 250/376
See application file for complete search history.

(56) References Cited

U.S. PATENT DOCUMENTS 7,497,997 B2 * 3/2009 Glezer et al. .................. 422/504
2002/0110839 A1 8/2002 Bach et al.
(Continued)

FOREIGN PATENT DOCUMENTS

DE 102009016712 * 10/2014 ............. G01N 21/75
WO WO 2012/068499 5/2012

OTHER PUBLICATIONS

Carlborg, et al., "A packaged optical slot-waveguide ring resonator sensor array for multiplex label-free assays in Labs-on-chips", The Royal Society of Chemistry, Lab Chip, Feb. 2010, 10(3), pp. 281-290, Published online: Nov. 12, 2009.

Hawkins, et al., "Optofluidic waveguides: II. Fabrication and structures", Microfluid Nanofluidics, (2008) 4(1-2),17-32, Jul. 19, 2007.
(Continued)

*Primary Examiner* — Tarifur Chowdhury
*Assistant Examiner* — Sunghee Y Gray
(74) *Attorney, Agent, or Firm* — Baker & Hostetler LLP

(57) ABSTRACT

An optofluidic platform is constructed to comprise a vertical integration of optical and fluidic layers. The optical layer enables interaction of light with a fluid for a variety of purposes, including particle detection, manipulation, and analysis. The vertical integration allows layers to be permanently or temporarily attached to each other. Temporary attachments provide the advantage of reusing the same optical layer with different fluidic layers. Most preferably, the optical layer comprises antiresonant reflecting optical waveguide. Further, a fluidic layer can be configured to act as an interface between the optical layer and other fluidic layers attached thereon. Moreover, the fluidic layers can be configured to perform fluidic functions. The optofluidic platform can also comprise a protective layer. As such, a liquid solution can be introduced in the optofluidic platform and single particles contained therein can be optically detected with extremely high sensitivity and without the need for advanced microscopy equipment.

40 Claims, 5 Drawing Sheets

(51) Int. Cl.
*G02B 6/00* (2006.01)
*G01N 21/01* (2006.01)
*B01L 3/00* (2006.01)
*G01N 21/03* (2006.01)
*G01N 21/77* (2006.01)
*G01N 21/64* (2006.01)

(52) U.S. Cl.
CPC .. *B01L2200/0647* (2013.01); *B01L 2200/0668* (2013.01); *B01L 2300/0654* (2013.01); *B01L 2300/0822* (2013.01); *B01L 2300/0877* (2013.01); *G01N 21/7703* (2013.01); *G01N 2021/6482* (2013.01); *Y10T 29/49826* (2015.01)

(56) References Cited

U.S. PATENT DOCUMENTS

| | | | |
|---|---|---|---|
| 2003/0096310 A1* | 5/2003 | Hansen et al. | 435/7.1 |
| 2004/0252957 A1 | 12/2004 | Schmidt et al. | |
| 2006/0008227 A1* | 1/2006 | Schmidt et al. | 385/129 |
| 2006/0171654 A1 | 8/2006 | Hawkins et al. | |
| 2012/0040470 A1* | 2/2012 | Dorn et al. | 436/169 |

OTHER PUBLICATIONS

International Patent Application No. PCT/US2011/061463: International Search Report and Written Opinion dated Jul. 23, 2012, 14 pages.

\* cited by examiner (a)

(b)

(a)

(b)

(a)

(b)

HYBRID, PLANAR OPTOFLUIDIC INTEGRATION

CROSS-REFERENCE TO RELATED APPLICATIONS

This application is the National Stage of International Application No. PCT/US2011/061463, filed Nov. 18, 2011, which claims the benefit of U.S. Provisional Application No. 61/415,467, filed Nov. 19, 2010, the disclosures of which are incorporated herein by reference in their entireties.

TECHNICAL FIELD

The present invention relates generally to the field of integrated optics, and more particularly to an optofluidic platform for optical particle detection without the need for advanced microscopy equipment. The optofluidic platform comprises a vertical integration of an optical layer and a plurality of fluidic layers. The optical layer can employ antiresonant reflecting optical waveguides, known as ARROWs or ARROW waveguides. Further, the fluidic layer can be configured to perform fluidic functions on liquids introduced into the optofluidic platform. The optofluidic platform can also comprise a protective layer.

BACKGROUND

Optofluidics is a rapidly growing field that deals with the interplay of optics and fluids, typically liquids, at the microscale. Currently, the major research trends include optical devices defined by fluids, optical particle manipulation in liquids, and optical particle detection and analysis, especially in biology and biomedicine.

It has been pointed out that one of the main advantages of an optofluidic approach is the possibility to vertically combine layers with different functionalities in a single device. Proof-of principle demonstrations include fluidically tunable waveguide transmission [1] and combination of electrical and fluidic layers [2].

SUMMARY

Here, we describe a novel approach to optofluidic integration based on liquid-core waveguides. Its novel features are:
- use of liquid-core waveguide layer featuring fully planar optical beam paths for vertical integration
- use of dissimilar materials to achieve desired functionalities in individual layers. Examples include silicon, PDMS, glass;
- reconfigurable assembly of vertically integrated optofluidic system.

In a presently preferred embodiment of the invention, an optofluidic platform is constructed so as to comprise a vertical integration of optical and fluidic layers. The optofluidic platform can also comprise a protective layer. The vertical integration allows layers to be permanently or temporarily attached to each other. Temporary attachments provide the advantage of reusing the same optical layer with different fluidic layers.

In an embodiment, the optical layer can comprise a self-contained, planar optofluidic platform for optical particle detection with extremely high sensitivity but without the need for advanced microscopy equipment. In a further embodiment, the optical layer can comprise hollow-core antiresonant reflecting optical waveguides (ARROWs), solid-core ARROWs, and fluidic reservoirs. The configuration of the different components within the optical layer can allow liquids to be introduced into the hollow-core ARROWs and sub-picoliter volumes thereof to be optically excited for single particle detection.

In an embodiment, a fluidic layer can be attached to the optical layer and can act as a gasket that provides a seal for liquids between the protective layer and the optical layer. In a further embodiment, the fluidic layer attached to the optical layer can be configured to restore the optical waveguide properties of the optical layer and can act as an interface layer between the optical layer and other fluidic layers attached thereon. Additionally, the fluidic layers can be configured to perform fluidic functions, such as filtering and distributing to the optical layer liquids introduced at the protective layer.

In an embodiment, the protective layer can be attached to a fluidic layer. The protective layer can be configured to introduce liquids into the optofluidic platform using syringes and syringe pumps.

In an embodiment, the optical layer can be fabricated by depositing dielectric layers on a silicon substrate, using a sacrificial material to pattern a desired hollow-shape, covering the sacrificial material with additional dielectric layers, and using chemical etching to remove the sacrificial materials. Additionally, a fluidic layer can be made of polydimethylsiloxane, polymers, or glass materials. The protective layer can be made of acrylic glass. These layers can be permanently connected via standard oxygen plasma bonding or can be assembled with a temporary fixture under pressure.

Other aspects of illustrative embodiments of the invention are described below.

DETAILED DESCRIPTION OF ILLUSTRATIVE EMBODIMENTS

We have invented a planar, optofluidic approach that is based on liquid-core optical waveguides that maximizes the interaction between light and sample analytes. Based on creating hollow-core antiresonant reflecting optical waveguides (ARROWs), we have developed a self-contained, planar optofluidic platform for optical particle detection with extremely high sensitivity but without the need for advanced microscopy equipment [3]. The basic layout of this platform along with the fabrication steps for forming the hollow-core waveguides are shown in FIG. 1.

Figure 1:
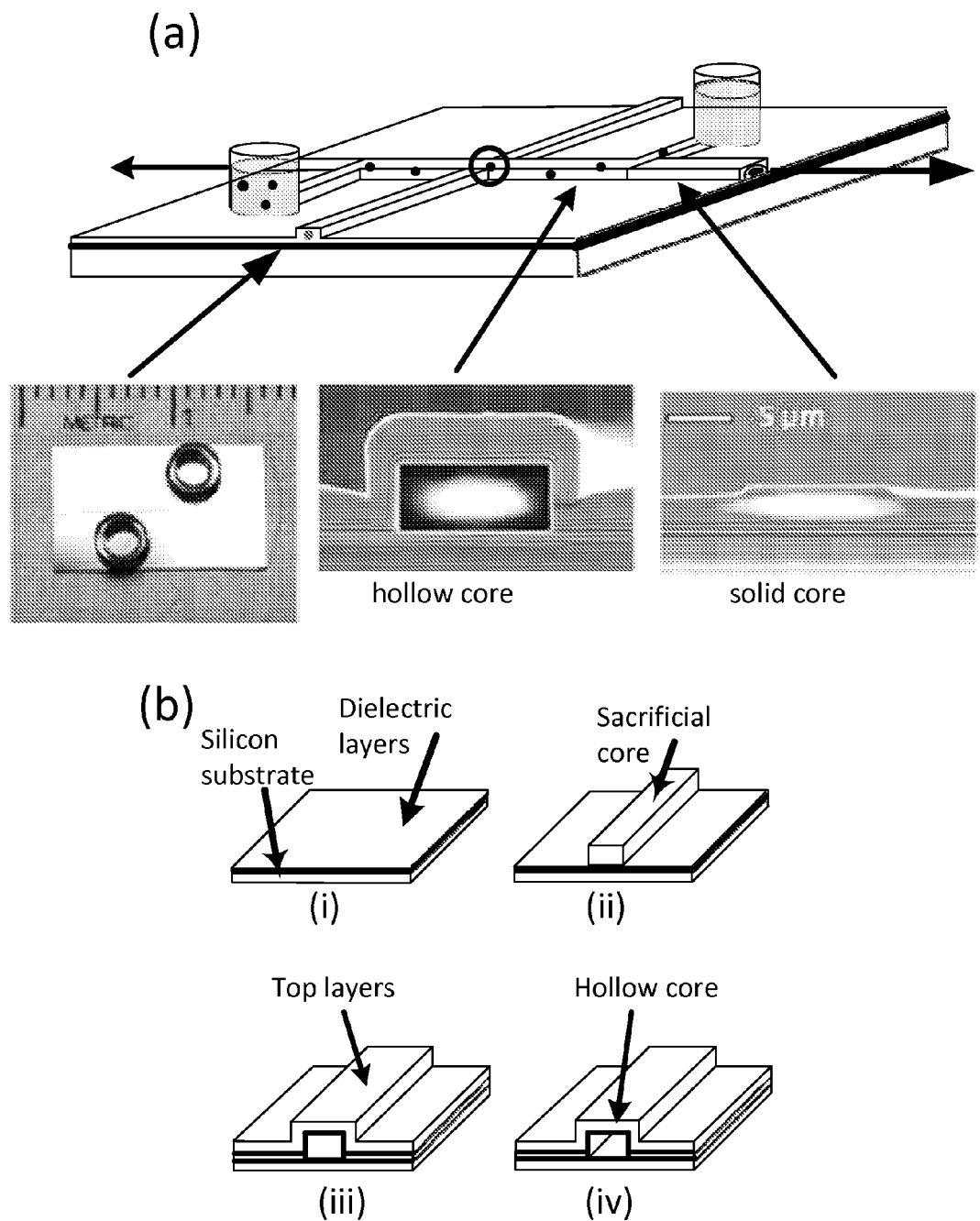
FIG. 1 shows a planar optofluidic platform; (a) shows a schematic layout, images of waveguide cross sections and completed chip; (b) shows a key microfabrication process steps for creating liquid core waveguides.

The scanning electron image in the bottom center of FIG. 1 shows a cross section of such a waveguide with hollow-core dimensions of 5×12 μm. In addition, solid-core ARROW waveguides (see SEM in bottom right of FIG. 1a) are connected to different points of the liquid core. This creates separate access paths for liquids and light into the main channel, and can also be used to define optical excitation areas with sub-picoliter volumes to achieve single molecule sensitivity. FIG. 1a depicts a typical experimental layout in which excitation light (green; arrow pointing into the optofluidic platform) enters the liquid core through an orthogonally intersecting solid-core ARROW. Generated light (red; arrow pointing out from the optofluidic platform) is collected perpendicularly in the chip plane and guided to the chip edges for detection. Fluidic reservoirs at the channel ends allow for easy channel filling and insertion of electrodes to induce electrokinetic particle movement. The photograph in the bottom left of FIG. 1a illustrates the compact size of a completed optofluidic chip.

The fabrication process shown in FIG. 1b includes (i) deposition of dielectric layers (e.g. SiO2 and SiN) of the correct thickness on a silicon substrate; (ii) patterning of a sacrificial material (e.g. SU-8) into the desired hollow-core shape; (iii) covering the sacrificial layer with additional ARROW guiding layers; and (iv) removal of the sacrificial core with chemical etching after exposing ends by plasma etching. It can be used flexibly to define a variety of optical and fluidic layouts with microscale precision.

The platform depicted in FIG. 1 has successfully been used for detection and analysis of a variety of molecules, including fluorescence detection of single dye molecules, fluorescence correlation analysis of liposomes and ribosomes, and surface-enhanced Raman detection of rhodamine 6G molecules [3].

Figure 2:
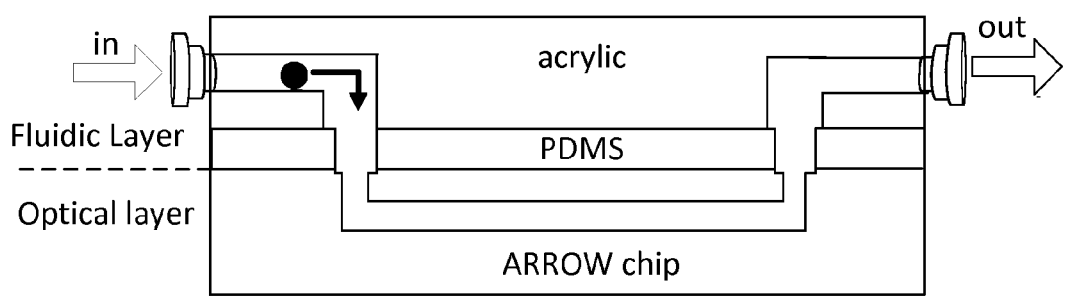
FIG. 2 shows integration of a fluidic layer; (a) shows a schematic side view of optofluidic layer sequence; (b) shows a top view of completed assembly with Luer connections; (c) shows a fluorescence image of quantum dots pipeted into one PDMS opening and vacuumed through liquid-core waveguide into opposing opening.
Figure 2:
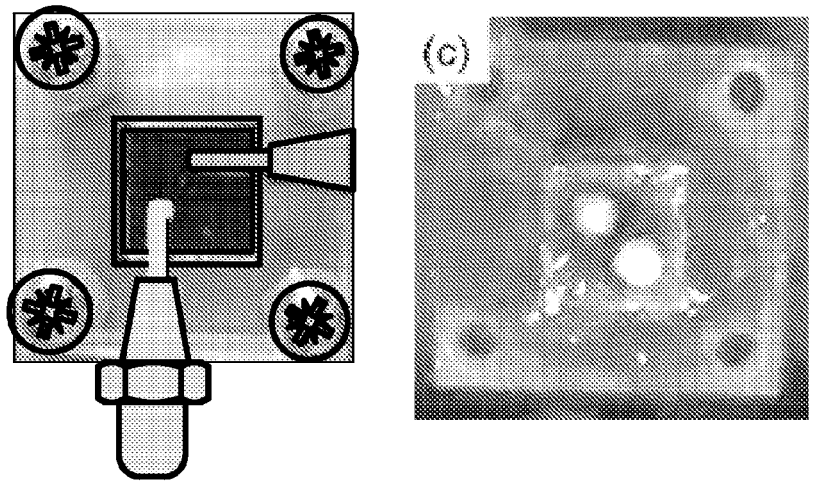

We have also carried out a proof-of-principle study on hybrid vertical alignment of optofluidic layers. The key intention was to establish that the silicon-based ARROW chip can be combined with materials such as polydimethylsiloxane (PDMS), polymers, or glass that are traditionally used for microfluidic devices. FIG. 2a shows a side view schematic of this test approach. A PDMS layer is attached on top of the ARROW chip followed by a cover of acrylic plastic. This PDMS layer acts as a gasket that provides a seal for liquids between the acrylic and silicon layers by conforming to the elevated waveguide structures on chip (see FIG. 1).

In order to achieve this function, PDMS was prepared in accordance with standard soft lithography methods and poured directly onto the ARROW chip. Temporary standoff cylinders were placed over the openings to the liquid-core ARROW to create through holes in the PDMS and removed after the PDMS was thermally cured. Channels were drilled into the acrylic piece and terminated with Luer connection for introduction of liquids into the liquid-core waveguides using syringes and syringe pumps. (FIG. 2b). FIG. 2c shows a top down image of the chip without the top acrylic piece. Fluorescent dye was introduced into one of the PDMS holes and vacuumed through the waveguide into the opposite opening. The observation of bright red fluorescence only in the two reservoirs demonstrates that this basic microfluidic functionality was successfully implemented without any leaks between PDMS and ARROW chip.

Figure 3:
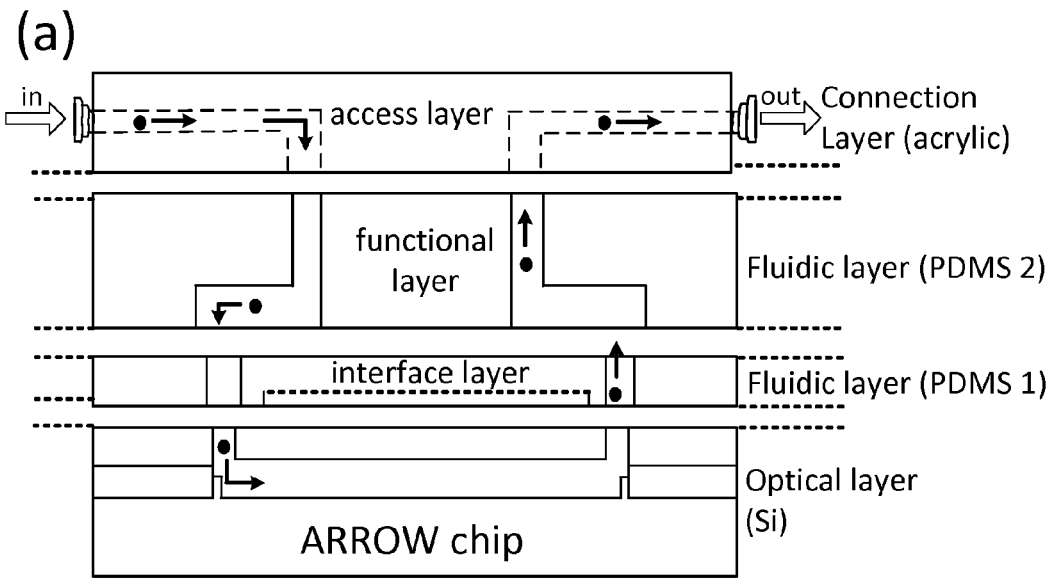
FIG. 3 shows a vertical optofluidic integration; (a) shows a schematic side view of multilayer hybrid optofluidic integration with dedicated functional optical and fluidic layers (dashed lines: channels; particle flow as indicated); (b) shows a cross-sectional view of structure showing air gaps in PDMS layer 1 to maintain optical waveguiding.
Figure 3:
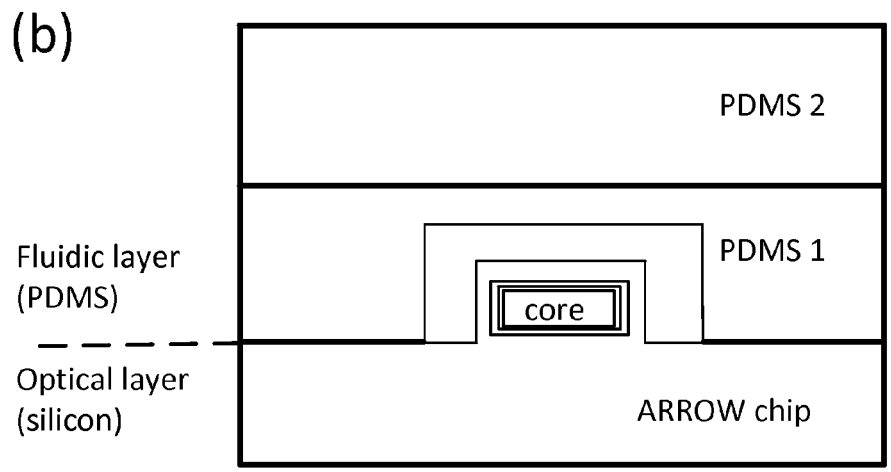

A multilayered approach to optofluidic integration has the advantage that each layer can be optimized for its desired functionality. While our silicon-based devices have shown excellent optical properties, they are not ideal from a packaging standpoint. One possible preferred approach to hybrid integration is to combine fluidic and optical layers in a single device as shown in FIG. 3a. The preferred implementation combines the silicon-based optical layer with two fluidic layers of soft polydimethylsiloxane (PDMS), capped by a hard access layer (e.g. acrylic plastic) for attaching fluidic connections (syringes, pumps). These layers can either be permanently connected via standard oxygen plasma bonding or can be assembled with a temporary fixture under pressure. The latter approach has the advantage that layers can be swapped, e.g. different fluidic channel designs can be used with a single optical chip.

Direct casting of PDMS on an ARROW chip has the disadvantage of placing high-refractive-index PDMS on top of the ARROW waveguides and destroying the optical waveguiding properties. The multilayer approach overcomes this problem since the first PDMS layer will contain air channels that follow the shape of the waveguide geometry in the areas that are critical for optical guiding. This results in air gaps around the waveguides that restore the required index profile as illustrated in FIG. 3b.

Figure 4:
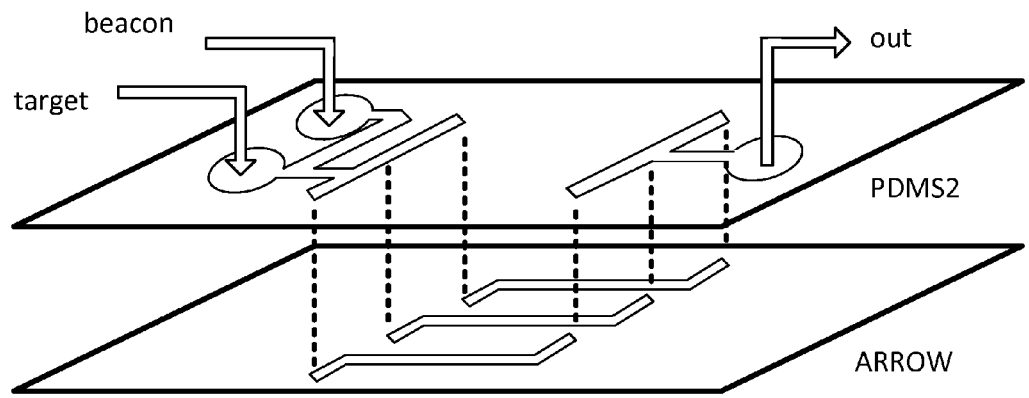
FIG. 4 shows a vertical optofluidic integration: sample delivery; (a) shows a sample mixed and distributed into three optical waveguides (white: microfluidic channels in PDMS layer); (b) shows three samples distributed into three optical waveguide channels. Note: PDMS 1 not shown for clarity.
Figure 4:
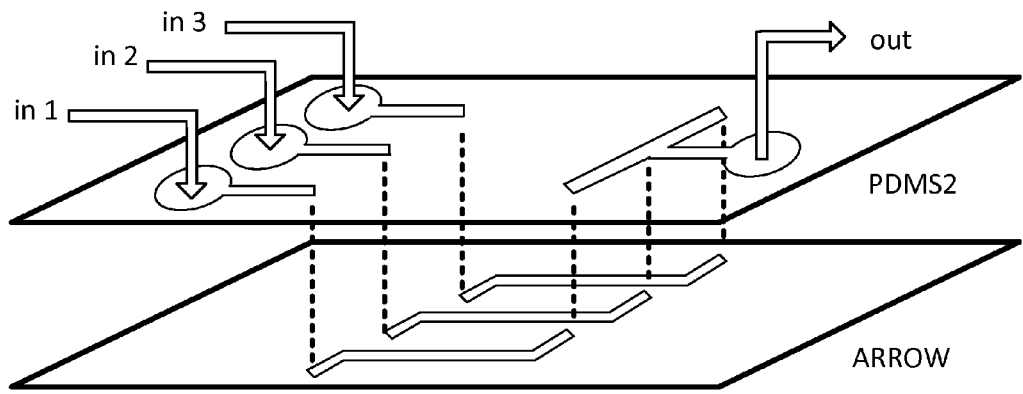

A second step can add the second PDMS layer (PDMS2) and demonstrate essential fluidic device functions in this layer such as sample distribution and mechanical filtration. FIG. 4 shows two preferred example implementations of sample distribution layouts (Note that PDMS1 layer is not shown for clarity). In FIG. 4a, the PDMS2 layer is designed as a 1-in-3 distributor for loading three ARROW waveguides with the same sample mixture. FIG. 4b, on the other hand, represents a 3-in-3 input configuration where three different sample mixtures can be investigated in three waveguide channels simultaneously. Both implementations enable multiplexing capabilities of the detection platform, albeit in different ways. Many more configurations are conceivable, in particular as the number of liquid-core waveguides grows. Note again that very different functionality is achieved with the same underlying optical ARROW layer. When the device is assembled without permanent bonding, this makes the platform highly customizable and reconfigurable.

Figure 5:
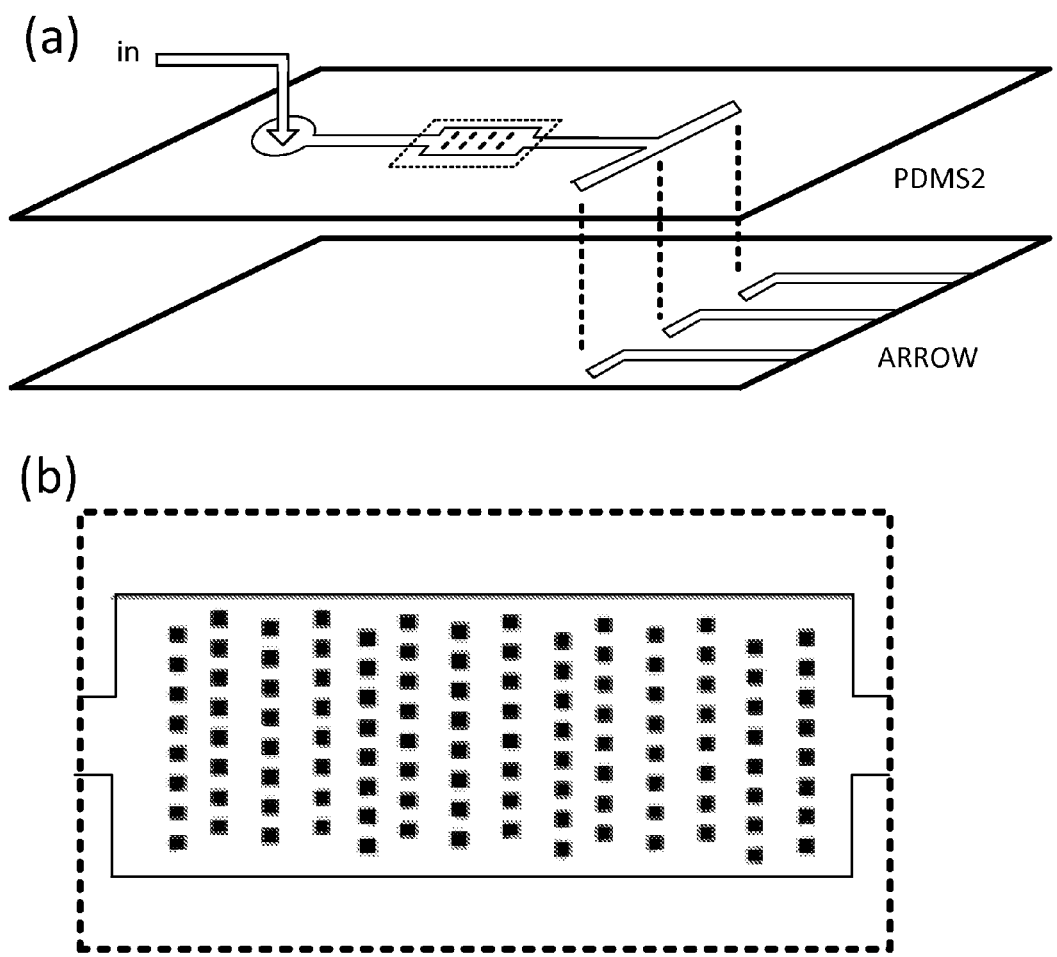
FIG. 5 shows a vertical optofluidic integration: sample filtering; (a) shows an overview of filter location (dashed parallelogram) in fluidic layer; (b) shows a close-up view of the filter section with PDMS posts providing mechanical barriers for large analyte components.

Sample preparation is a constant concern in microfluidic systems. One example for such a functionality is a mechanical fluidic filtering step that separates large cell components from molecular level targets after an off-chip lysing process. The constraints in our case are set by the liquid-core waveguide dimensions in the optical layer which are typically on the order of 5×12 μm. In order to remove all analyte contents larger than 3 μm, a pillar-based filter structure can be added to the input manifold in the PDMS2 layer as shown in FIG. 5. The necessary resolution of a few microns can be easily achieved using SU-8 mold lithography.

What is claimed is:

1. An optofluidic apparatus for analyzing samples and detection of individual particles, comprising:
    an optical layer comprising a plurality of waveguides;
    a plurality of fluidic layers, wherein a first fluidic layer of the plurality of fluidic layers is attached to the optical layer and is configured as an interface layer, and a second fluidic layer of the plurality of fluidic layers is attached to the first fluidic layer and is configured as a functional fluidic layer, wherein a first function of the second fluidic layer comprises distributing samples to the plurality of waveguides, and wherein a second function of the second fluidic layer comprises mechanical filtration of samples; and a protective layer attached to a fluidic layer of the plurality of fluidic layers;

wherein the optical layer is made of a different substrate material than the plurality of fluidic layers; and wherein the optical layer, plurality of fluidic layers, and protective layer are vertically integrated, and wherein light and individual particles in flow propagate through a channel of a fluidic layer such that the individual particles experience the full optical intensity of the light.

2. The apparatus of claim 1, wherein the plurality of waveguides comprises a plurality of hollow-core waveguides and a plurality of solid-core waveguides.

3. The apparatus of claim 1, wherein the plurality of waveguides comprises a plurality of hollow-core antiresonant reflecting optical waveguides (ARROWs).

4. The apparatus of claim 3 further comprising a plurality of solid-core ARROWs intersecting the plurality of hollow-core ARROWs.

5. The apparatus of claim 4, wherein the plurality of solid-core ARROWs and the plurality of hollow-core ARROWs intersect perpendicularly.

6. The apparatus of claim 4, wherein the plurality of hollow-core ARROWs and the plurality of solid-core ARROWs are configured to provide separate access paths for liquids and light and to define optical excitation areas with sub-picoliter volumes to achieve single molecule sensitivity.

7. The apparatus of claim 3, wherein a hollow-core ARROW has a substantially rectangular hollow-core with cross section dimensions of 5 μm×12 μm.

8. The apparatus of claim 3, wherein a hollow-core ARROW comprises a silicon substrate and a plurality of dielectric layers configured to form a hollow-core shape.

9. The apparatus of claim 3, wherein fluidic reservoirs are located at ends of a hollow-core ARROW.

10. The apparatus of claim 1, wherein the first fluidic layer is configured to provide an air gap between at least one waveguide and the first fluidic layer in areas used for optical guiding.

11. The apparatus of claim 1, wherein the plurality of fluidic layers are made of polydimethylsiloxane, polymers, or glass materials.

12. The apparatus of claim 1, wherein the plurality of fluidic layers comprises openings configured to channel liquids in and out of the plurality of waveguides.

13. The apparatus of claim 1, wherein the plurality of fluidic layers are configured to act as a gasket that provides a seal for liquids between the optical layer and a protective layer.

14. The apparatus of claim 1, further comprising distribution points for loading the plurality of waveguides with samples.

15. The apparatus of claim 1, wherein the second fluidic layer comprises a pillar-based filter structure for filtering sample contents.

16. The apparatus of claim 1, wherein the first fluidic layer and the optical layer are permanently attached.

17. The apparatus of claim 16, wherein the permanent attachment comprises oxygen plasma bonding.

18. The apparatus of claim 1, wherein the first fluidic layer and the optical layer are temporarily attached.

19. The apparatus of claim 18, wherein the temporary attachment comprises pressure bonding.

20. The apparatus of claim 1, wherein attachment of the first fluidic layer to the second fluidic layer comprises a permanent or a temporary attachment.

21. The apparatus of claim 1, wherein the protective layer is made of acrylic plastic.

22. The apparatus of claim 1, wherein the protective layer comprises channels for introducing liquids.

23. The apparatus of claim 22, wherein the channels are terminated with Luer connections configured for use with syringes and syringe pumps.

24. The apparatus of claim 1, wherein the attachment of the protective layer to a fluidic layer of the plurality of fluidic layers comprises a permanent or a temporary attachment.

25. The apparatus of claim 1 further being configured to provide a compact-size, self-contained, and planar optofluidic platform for optical particle detection.

26. A method for manufacturing an optofluidic device configured for detection of individual particles, comprising:
creating an optical layer comprising waveguides;
creating a plurality of fluidic layers;
creating a protective layer;
attaching the optical layer to a fluidic layer of the plurality of fluidic layers; and
attaching a fluidic layer of the plurality of fluidic layers to the protective layer;
wherein the optical layer, plurality of fluidic layers, and protective layer are vertically integrated, and wherein light and individual particles in flow propagate through a channel of a fluidic layer such that the individual particles experience the full optical intensity of the light;
wherein the optical layer is made of a different substrate material than the plurality of fluidic layers; and
wherein a first fluidic layer of the plurality of fluidic layers is attached to the optical layer and is configured as an interface layer, and a second fluidic layer of the plurality of fluidic layers is attached to the first fluidic layer and is configured as a functional fluidic layer, wherein a first function of the second fluidic layer comprises distributing samples to the plurality of waveguides, and wherein a second function of the second fluidic layer comprises mechanical filtration of samples.

27. The method of claim 26, wherein creating the optical layer comprises:
depositing dielectric layers on a silicon substrate;
patterning a material into a waveguide hollow-core shape;
covering the material with additional dielectric layers; and
removing the material.

28. The method of claim 27, wherein removing the material comprises exposing ends of the material to plasma etching and removing the material by chemical etching.

29. The method of claim 26, wherein creating a plurality of fluidic layers comprises:
covering openings of the waveguides with temporary standoff cylinders;
preparing a material using soft lithography methods;
pouring the prepared material onto the optical layer;
curing the poured material; and
removing the temporary standoff cylinders.

30. The method of claim 29, wherein the material comprises polydimethylsiloxane, polymers, or glass materials.

31. The method of claim 26, wherein creating the plurality of fluidic layers comprise creating at least one fluidic layer configured to be attached to the optical layer, the at least one fluidic layer being configured to provide air gaps between the waveguides and the at least one fluidic layer.

32. The method of claim 26, wherein creating the plurality of fluidic layers comprises creating at least one fluidic layer configured to be attached to the protective layer, the at least one fluidic layer configured to perform fluidic functions comprising distribution of samples to the waveguides, filtering of sample contents, or a combination thereof.

33. The method of claim 26, wherein creating the plurality of fluidic layers comprises configuring at least a fluidic layer to act as a gasket that provides a seal for liquids between the protective layer and the optical layer.

34. The method of claim 26, wherein creating the protective layer comprises using acrylic plastic for the protective layer.

35. The method of claim 26, wherein creating the protective layer comprises drilling channels in the protective layer and terminating the channels with Luer connections, the channels and Luer connections being configured to introduce liquids into the waveguides using syringes and syringe pumps.

36. The method of claim 26, wherein attaching the optical layer to the fluidic layer comprises a permanent or a temporary attachment.

37. The method of claim 36, wherein the permanent attachment comprises oxygen plasma bonding.

38. The method of claim 36, wherein the temporary attachment comprises pressure bonding.

39. The method of claim 26, wherein attaching the fluidic layer to the protective layer comprises a permanent or a temporary attachment.

40. The method of claim 26, wherein creating the plurality of fluidic layers comprises permanently or temporarily attaching each fluidic layer to another fluidic layer.

* * * * *